United States Patent [19]

Kyle

[11] Patent Number: 4,518,820

[45] Date of Patent: May 21, 1985

[54] TERMINAL ASSEMBLY FOR HEART PACEMAKERS

[76] Inventor: James C. Kyle, 2547 Fisher Rd., Roseburg, Oreg. 97470

[21] Appl. No.: 439,048

[22] Filed: Nov. 4, 1982

[51] Int. Cl.$^3$ .................................... H01B 17/26
[52] U.S. Cl. .................... 174/152 GM; 128/419 P
[58] Field of Search ............ 174/50.61, 151, 152 GM; 128/419 P

[56] References Cited

U.S. PATENT DOCUMENTS 2,318,435  5/1943  Stupakoff et al. .......... 174/152 GM

*Primary Examiner*—Laramie E. Askin
*Attorney, Agent, or Firm*—Ellsworth R. Roston; Charles H. Schwartz

[57] ABSTRACT

A ferrule made from an electrically conductive material has a coefficient of thermal expansion which changes at a particular rate with temperature changes. The ferrule is attached to an electrically conductive lid as by the application of heat and has a body portion pivotally movable at a particular position, such as a heat sink, on the body portion. Such heat sink has a minimal thickness in the body portion. When the ferrule is being attached to the lid as by heat, the heat becomes concentrated in the ferrule at the heat sink. A first ceramic material disposed within the ferrule has hard and rigid properties and is supported by the ferrule above the heat sink. The first ceramic material is preferably fused partially to the ferrule to provide for variations in its pivotal disposition relative to the ferrule. A second ceramic material within the ferrule is fused to the ferrule and the first ceramic material. The second ceramic material has more amorphous properties than the first ceramic material. The second ceramic material has a coefficient of thermal expansion which changes at substantially the particular rate with changes in temperature. Insulating material on the second material is fused to such ceramic material. The insulating material has a coefficient of thermal expansion which changes at substantially the particular rate with temperature changes. The insulating material isolates a plurality of terminal pins electrically to prevent the formation of dendrites between the pins. The pins extend through the ferrule and the lid.

24 Claims, 4 Drawing Figures

TERMINAL ASSEMBLY FOR HEART PACEMAKERS

This invention relates to heart pacemakers and more particularly relates to terminal assemblies for heart pacemakers. The invention especially relates to terminal assemblies for heart pacemakers of small size, particularly to those where a multiple number of leads extend from the terminal assembly coupled to the lid of heart pacemakers.

Heart pacemakers are carried by patients to regulate the heartbeat of the patient. Initially, the pacemakers were worn externally by the patient. Leads then extended internally into the patient from the pacemaker to the patient's heart to regulate the heart beat of the patient. The pacemakers were large and heavy and they did not have a long life. They accordingly had to be replaced fairly often with resultant discomforts, and even danger, to the patient.

The pacemakers subsequently became improved so that they could be inserted into the patient's body. This eliminated the inconvenience to the pateint of having to wear the pacemaker externally but it tended to decrease the life of the pacemaker because the human body generates chemicals which are deleterious to foreign objects, such as pacemakers, in the body.

Advances were then made in pacemakers to increase the life of the pacemaker in the patient's body and to decrease the size of the pacemaker. Such advances have been particularly make in the assembly which is connected to a lid forming a part of the pacemaker casing and which is constructed to provide for connections from the pacemaker to the patient's heart. Such advances have been particularly important because the area around the lid is the critical area where leaks often tend initially to appear.

As medical knowledge has advanced, decisions have been made to increase the number of connections from the heart pacemaker to the patient's heart. This has occurred because the heart has four (4) sections, two (2) ventricles and two (2) auricles. Thus, one (1) connection was initially made to the heart from the pacemaker and then two (2) connections were made. These connections become possible because of the advances being made in the pacemakers, and particularly in the terminal assembly for the lid, even though the size of the pacemakers was being decreased as the number of terminals were being increased.

The size of the heart pacemakers has now been decreased so that the pacemakers are sub-miniature, particularly in comparison to their original size. At the same time, four (4) terminals from the pacemaker for connection to the four (4) sections of the heart are being specified. However, because four (4) terminals are required in a package of sub-miniature size, it has been difficult to provide a satisfactory terminal assembly. This has been so even though considerable effort and money have been expended in recent years to overcome the difficulties specified above.

This invention provides a terminal assembly for the lid of a sub-miniature pacemaker. The terminal assembly is effective in maintaining the lid sealed even when the pacemaker is installed in the body for years. The terminal assembly maintains this sealed relationship even when considerable amounts of heat are applied to the terminal assembly to seal the assembly to the lid. The terminal assembly is effective in providing for the introduction of four (4) different electrical leads from the pacemaker to the patient's heart and for maintaining a high electrical resistivity between the different terminals in the pacemaker and between the different terminals and the ground represented by the casing for the pacemaker.

In one embodiment of the invention, a lid and a ferrule are preferably made from electrically conductive materials. The ferrule is also preferably made from a material having a coefficient of thermal expansion which changes at a particular rate with changes in temperature. The ferrule is attached to the lid as by the application of heat and is provided with a body portion constructed for pivotal movement at a particular position, such as a heat sink, along the body portion. Such heat sink is defined by a position of minimal thickness in the body portion. When the ferrule becomes attached to the lid as by heat, the heat becomes concentrated in the ferrule at the position of the heat sink.

A first ceramic material disposed within the ferrule has hard and rigid properties and is supported by the ferrule at a position above the heat sink. The first ceramic material is preferably fused partially to the ferrule to provide for variations in its pivotal disposition relative to the ferrule.

A second ceramic material in the ferrule is fused to the ferrule and the first ceramic material. The second ceramic material has more amorphous properties than the first ceramic material. The second ceramic material has a coefficient of thermal expansion which changes at substantially the particular rate with changes in temperature.

Insulating material on the second ceramic material is fused to the second ceramic material. The insulating material has a coefficient of thermal expansion which changes at substantially the particular rate with changes in temperature. The insulating material is constructed to isolate a plurality of terminal pins electrically and to prevent the formation of dendrites between the pins. The pins extend through the ferrule and the lid.

Figure 1:
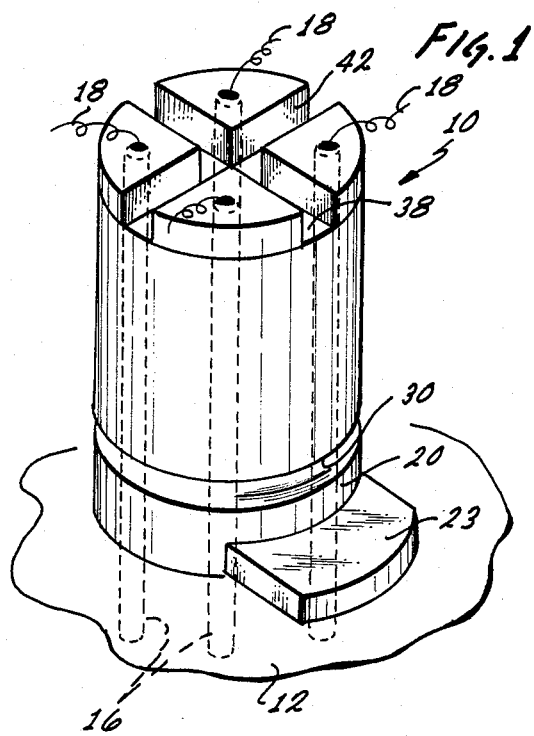
FIG. 1 is a schematic perspective view of a terminal lid assembly constituting one embodiment of the invention.

In one embodiment of the invention, an assembly generally indicated at 10 is provided for use with heart pacemakers installed inside a patient's body. The assembly 10 includes a lid 12 for the heart pacemaker. The lid may be made from a suitable material such as titanium, a titanium alloy or stainless steel. The lid 10 includes an aperture 14 for receiving terminal pins 16. The terminal pins 16 may be made from a suitable material such as platinum, steel, titanium or a metal such as steel coated with platinum. As many as four (4) terminal pins 16 may be provided to introduce signals to the two (2) auricles and the two (2) ventricles of the patient's heart. When four (4) terminal pins 16 are provided, a lead 18 may be connected from each individual one (1) of the pins to a different one of the auricles or ventricles.

A ferrule 20 made from a suitable material such as titanium or a titanium alloy is suitably attached as at 21 to the lid 12. This attachment may be provided by the application of heat such as by a laser, an electronic beam or other means known in the art. The ferrule 20 is preferably provided with a projection 22 on a flange portion 23 to facilitate the attachment of the ferrule to the lid 12 as by heat.

A hollow cylindrical body 24 extends from the flange portion 23, preferably at right angles to the flange portion. The cylindrical body 24 has an internal shelf 26 at an intermediate position along the height of the body 24. The shelf 26 is defined by an increased thickness of the body 24 below the shelf relative to the thickness of the body above the shelf. A heat sink 30 is provided on the exterior surface of the body at a position intermediate the flange portion 23 and the shelf 26. The heat sink 30 is defined by a cut in the body 24, preferably with a semi-cylindrical configuration.

A ceramic material 32 is disposed on the shelf 26. The ceramic material 32 has hard and rigid properties and is resistant to sudden and sharp mechanical forces and stresses. This results from the fact that the material 32 is substantially crystalline. The ceramic material 32 has a melting temperature significantly above 1280° F., which is approximately the temperature at which the different components in the assembly 10 are heated after they have been assembled. Since this temperature is below 1350° F., the temperature at which titanium oxidizes, the material 32 does not become fused to the ferrule 20 at positions 33 along the shelf 26. The material 32 does not become fused to the ferrule 20 at these positions because the fusing generally occurs to an oxide layer on the surface of the ferrule.

Figure 2:
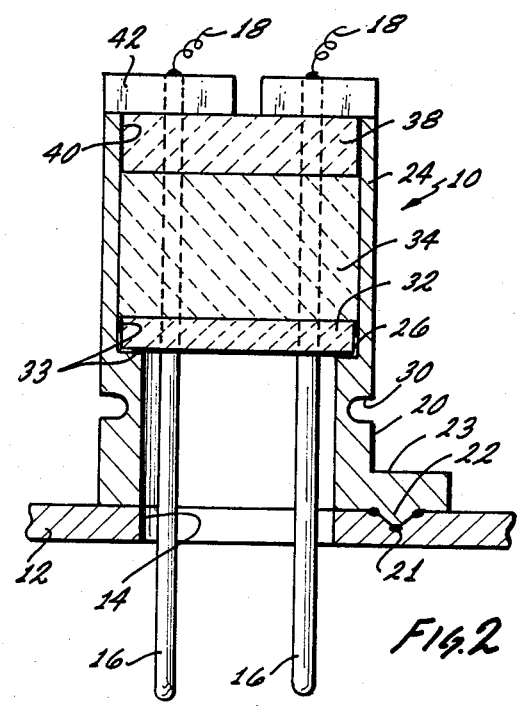
FIG. 2 is an enlarged elevational view, in section, of the terminal assembly shown in FIG. 1.
Figure 3:
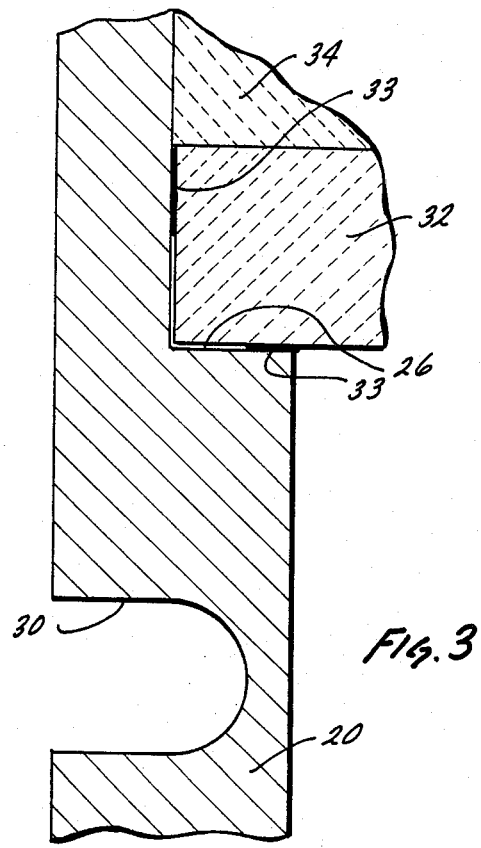
FIG. 3 is a fragmentary view, in even further enlarged section, of certain of the elements shown in FIGS. 1 and 2.

An insulating material generally indicated at 34 in FIGS. 2 and 3 is disposed within the ferrule 20 on the ceramic material 32. The insulating material 34 is fused to the ceramic material 32 and to the ferrule 20. This fusing can occur at a temperature of approximately 1280° F. because the ceramic material 34 is provided with lower melting and fusing temperatures than the material 32. The insulating material 34 is partially amorphous and partially crystalline. At least partially because of this, the material 34 can be hermetically sealed to the ferrule 20 and the material 32 in a subsequent reheating if a hermetic seal is not produced in a previous heating. The insulating material 34 has a coefficient of thermal expansion which changes at substantially the same rate as that of the ferrule 20 with changes in temperature. The insulating material 34 has the properties of forming a eutectic with the material 32 at the boundaries between the materials 32 and 34. The formation of this eutectic at the boundary between the materials 32 and 34 enhances the bond of the material 34 with the material 32.

Figure 4:
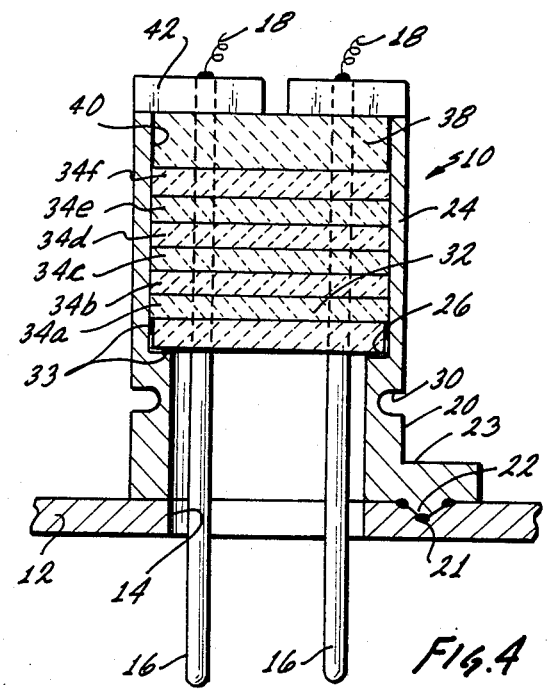
FIG. 4 is a fragmentary enlarged elevational view, in section, of a terminal assembly constituting another embodiment of the invention.

Actually, as shown in FIG. 4, the material 34 may constitute a plurality of layers 34a, 34b, 34c, etc. each having a progressive change in properties. Each of the layers 34b, 34c, etc., is further removed from the material 32 than the layers 34a, 34b, etc., is more amorphous than the layers 34a, 34b, etc. and is provided with lower melting and fusing temperatures than the layers 34a, 34b, etc. The layers 34a, 34b, 34c, etc., are preferably formed from the same materials but in different proportions. By providing the layers 34a, 34b, 34c, etc. with progressive characteristics, fusion of the layers 34a, 34b, 34c, etc. to one another and to the ferrule 20 and the insulating material 32 is enhanced and is maintained even with sudden and sharp variations in temperature.

An insulating member 38 is disposed in the ferrule 20 and is hermetically sealed to the insulating material 34. The member 38 preferably has a coefficient of thermal expansion which varies at substantially the same rate with changes in temperature as the ferrule 20 and the material 34. The material forming the member 38 may be that designated by the trademark "Fosterite". It has a composition which includes magnesium oxide, silica and alumina. One common form of Fosterite may be obtained from Westman Ceramics and may have the following composition:

| Material | Percentage |
|---|---|
| Calcined Montana Talc | 15 |
| Raw Montana Talc | 18 |
| Kaolin | 16 |
| Bentonite | 1 |
| Magnesite | 50 |

A thin layer 40 having substantially the same composition as the material 34 may be disposed between the member 38 and the body 24 of the ferrule 20 to seal the member 38 and the ferrule. The combination of Fosterite, the material 34 and a ferrule made from titanium is fully disclosed and claimed in application Ser. No. 154,783 filed by me on May 30, 1980, now abandoned in favor of continuation application Ser. No. 419,625 filed Sept. 20, 1982.

The insulating member 38 may have grooves 42 on its external surface. The number of grooves is dependent upon the number of terminal pins 16 included in the assembly. For example, when four (4) terminal pins 16 are included, the grooves 42 may have a cruciform configuration. Each of the terminal pins 16 is disposed in a different one of the quadrants defined by the grooves 42. Each of the terminal pins 16 extends through the member 38 from a position external to the member and through the aperture 14 in the lid 12 for connection to strategic terminals in the heart pacemaker.

The material 32 may be formed in a manner similar to that disclosed and claimed in co-pending application Ser. No. 111,787 filed by me on Jan. 9, 1980, abandoned in favor of continuation application Ser. No. 322,014 filed Nov. 16, 1981, now U.S. Pat. No. 4,461,926 and may be provided with properties and advantages similar to those disclosed and claimed in that application. The material 34 may be formed in a manner similar to that disclosed and claimed in co-pending application Ser. No. 229,151 filed by me on Jan. 28, 1981, now U.S. Pat. No. 4,421,947 and may be provided with properties and advantages similar to those disclosed and claimed in that application. The interrelationships of the material 32, the material 34, the material forming the member 38, the terminal pins 16 and the material forming the ferrule 20 are fully disclosed and claimed in co-pending application Ser. No. 154,783 (abandoned in favor of continuation application Ser. No. 419,625 filed Sept. 20, 1982). The materials 34a, 34b, 34c, etc. are fully disclosed and claimed in application Ser. No. 251,512 filed by me on Apr. 6, 1981, now U.S. Pat. No. 4,425,476, and the properties and advantages of such materials are fully disclosed and claimed in that application.

The materials 32 and 34 (or the materials 34a, 34b, 34c, etc.) may be separately formed as first described in the co-pending applications and may be assembled with the member 38 in the ferrule 20. This assembly may then be heated at a suitable temperature such as a temperature of approximately 1280° F. for a suitable period of time such as a period of about one half (½) hour to one (1) hour. This causes the material 34 to become fused to the material 32, the terminal pins 16 and the ferrule 20. However, the material 32 is not fused to the ferrule 20, at least along the corner area 33 of the shelf 26, because the temperature is below the temperature of approximately 1350° F. required to produce such fusion.

The ferrule 20 is then fused to the lid 12 by the application of heat. This heat is trapped by the heat sink 30 on the body 24. This heat causes the heat sink to expand and even to flex because of the high temperatures produced. The expansion and flexure can be obtained because the material 32 is not fused to the ferrule 20 at the corners of the shelf 26. In this way, an accommodation is provided between the different members in the sub-assembly of FIGS. 1, 2 and 3 even when the members are quite small. This accommodation causes the hermetic seal of the material 34 with the material 32, the member 38 and the ferrule 20 to be maintained even while ferrule 20 is being fused to the lid 12. By way of illustration, the member 38 may be provided with a diameter of approximately one eighth of an inch (⅛") and a heighth of approximately one sixteenth of an inch (1/16"). The other members in the sub-assembly constituting this invention may be provided with corresponding dimensions.

The insulating material 32 may be formed from the following materials in the following relative amounts by weight:

| Material | Relative Amount by Weight |
|---|---|
| Lead oxide (preferably red lead) | 455 |
| Zinc oxide | 40 |
| Alumina (preferably calcined) | 20 |
| Silicon dioxide | 300 |
| Cerium oxide | 10 |
| Lanthanum oxide | 30 |
| Cobalt oxide | 15 |
| Sodium antimonate | 80 |
| Zinc zirconium silicate | 30 |
| Bismuth trioxide | 100 |
| Molybdenum trioxide | 30 (but as low as 0.5% by weight) |

Oxides selected from a group consisting of the oxides of chromium, nickel and manganese may be substituted for the oxide of cobalt in the material 32. Oxides selected from a group consisting of the oxides of lithium and potassium may be substituted for the oxide of sodium. The oxide of lanthanum may be substituted for the oxide of cerium in the material 32. A material such as zinc zirconium silicate may be substituted for the oxide of zinc. However, all of such substitutions may cause the properties of the resultant insulating material to deteriorate slightly from the properties of the material obtained from the mixture specified above.

The insulating material 32 may be produced by a novel method. The different materials are initially weighted and milled and dried in a dry ball mill for an extended period of time such as approximately three (3) hours. The materials may then be placed in a mullite crucible preheated to a suitable temperature such as approximately 2200° F. The mixture may be heated in the preheated crucible at a suitable temperature such as a temperature of approximately 2200° F. for an extended period of time such as approximately six (6) hours. The mixture may thereafter be air cooled to a suitable temperature such as approximately 1000° F. The material may subsequently be heated in the mullite crucible to an elevated temperature such as approximately 2000° F. for an extended period such as approximately five (5) hours.

The smelted mixture may thereafter be fritted in deionized water and ground into particles in a suitable pulverizer which is non-contaminated. The particles may then be mixed with a suitable binder and may be pressed into beads which are then sintered at a suitable temperature such as approximately 1400° F. A suitable binder may be polyethylene glycol (marketed under the name "carbowax") or an animal fat. The beads may subsequently be disposed on the ledge 26 in the ferrule 20.

In the insulating material 32, the oxides of lead, silicon, bismuth and sodium constitute glass formers. The oxides of cerium, lanthanum, zinc and zirconium produce crystallites. These crystallites have different sizes and shapes to enhance the ability of insulating material to withstand different operating conditions. The amount of crystallites in the material may be in the order of eighty-five percent (85%) to ninety percent (90%) and the remainder of the material may be amorphous. The amorphous portion may be dispersed somewhat uniformly throughout the insulating material.

The oxides of zinc and aluminum tend to increase the viscosity of the insulating material 32. The oxide of aluminum also increases the melting temperature of the insulating material. In addition to producing crystallites, the oxide of cerium prevents the oxide of lanthanum from crystallizing too quickly or from crystallizing irregularly. As a result, the oxide of cerium is instrumental in providing homogeneity in the insulating material. The oxide of cobalt and the oxide of molybedenum enhance the bond of the insulating material to certain elements such as nickel, vanadium and chromium when the terminals pins 16 and the ferrule 20 are made from a suitable material such as an "INCONEL" alloy. The oxide of bismuth tends to promote high surface resistivity, thereby increasing the electrical resistance of the material. The oxide of bismuth also tends to prevent lead from leaching out of the material.

The material 34 includes a pair of fluxes having different melting temperatures. Preferably one of the fluxes has a melting temperature greater by several hundreds of degrees Fahrenheit, such as approximately 200° F. to 300° F. than the other flux. By way of illustration, one of the fluxes (Flux A) may have a melting temperature of approximately 800° F. and a composition as follows:

| Material | Relative Percentage By Weight |
|---|---|
| Lead oxide (PbO) | 68.5 |
| Boric oxide ($B_2O_3$) | 10.5 |
| Silicon dioxide ($SiO_2$) | 21.0 |

The other flux (Flux B) may have a melting temperature of approximately 1000° F. and a composition as follows:

| Material | Relative Percentage By Weight |
|---|---|
| Lead oxide (PbO) | 80.0 |

| Material | Relative Percentage By Weight |
| --- | --- |
| Boric oxide (B$_2$O$_3$) | 20.0 |

Fluxes A and B tend to constitute eutectics which effectively lower the melting point of the boric oxide in the fluxes.

When fluxes A and B are provided as specified above, flux A may have a relative percentage by weight in the material of approximately fifteen percent (15%) to twenty-five percent (25%) and flux B may have a relative percentage by weight in the material of approximately forty percent (40%) to fifty-five (55%). A stuffing material having properties of becoming crystalline is also provided in the material in a percentage by weight of approximately twenty percent (20%) to forty-five percent (45%).

The crystalline stuffing in the material 34 includes oxides of zinc and zirconium and silicon dioxide to provide for the formation of crystals in at least a portion of the material. The oxides of zinc and zirconium and the silicon dioxide may be included in such forms as zinc zirconium silicate, zirconium spinel and zirconium silicate. For example, the crystalline stuffing may be formed from the following materials in the following percentages by weight:

| Material | Relative Parts by Weight |
| --- | --- |
| Lead antimonate (Pb$_3$(SbO$_4$)$_2$) composed of lead, antimony and oxygen | 2 |
| Zinc zirconium silicate | 1 |
| Zirconium spinel | 1 |
| Zirconium silicate | 1 |

The crystalline stuffing specified above has particular utility in hermetically sealing pure titanium.

To form the material 34 and to produce hermetic seals with such material, fluxes A and B are first smelted separately and quenched in water to frit the material. For example, flux A may be smelted for a period of approximately two (2) hours at a temperature of approximately 1500° F. and then quenched in water, and flux B may be smelted for a period of approximately one (1) hour at a temperature of approxmately 1200° F. and then quenched in water. The crystalline stuffing is smelted for a period of approximately three (3) hours at a temperature of approximately 1800° F. and is then quenched in water.

The fritted fluxes and the crystalline stuffing are then mixed in the desired percentages and ground such as in a ball mill for a period of approximately three (3) to four (4) hours. The material is then heated to a temperature of approximately 1200° F. to 1300° F. for a period of approximately two (2) to three (3) hours. Preferably the material is stirred periodically such as every fifteen (15) minutes while it is being heated. The temperatures and times chosen for such heating operation are such as to partially combine the different compounds in the mixture. As a result, the material is predominantly amorphous but a portion has become crystalline. For example, approximately eighty percent (80%) of the material may be amorphous and approximately twenty percent (20%) may be crystalline. The material is then converted to a frit by quenching in water. The resultant material has a melting temperature of approximately 1100° F.

The material 34 is then heated to a temperature slightly above its melting temperature for a period of time dependent upon the characteristics desired for the material. For example, the material may be heated to a temperature of approximately 1200° F. (100° F. above the melting temperature) for a period of approximately three (3) to four (4) hours. The material slowly changes from an amorphous glass to a ceramic as it is being heated. Furthermore, the coefficient of thermal expansion of the material slowly decreases as the material becomes progressively crystalline.

The temperature and duration of the heating operation are chosen so that the coefficient of thermal expansion of the material is approximately the same as the coefficient of thermal expansion of the member, such as the ferrule 20, to be sealed. For example, when the ferrule 20 has a coefficient of thermal expansion of approximately seven (7), the material may be provided with a coefficient of thermal expansion of approximately seven and one-half (7.5). The temperature and duration of the heating operation are such that the material is approximately fifty percent (50%) amorphous and approximately fifty percent (50%) crystalline or slightly more crystalline than amorphous.

The fritted material is then pulverized and separated into different sizes. Beads are then formed by mixing particles of different sizes with a suitable material such as polyethylene glycol (marketed under the name "carbowax") or an animal fat and pressing the particles together. For example, approximately forty percent (40%) of particles by weight with 150 mesh, approximately fifty percent (50%) of particles with 300 mesh and approximately ten percent (10%) of particles above 300 mesh may be mixed with polyethylene glycol or an animal fat where the polyethylene glycol or the animal fat comprises one and one-half percent (1.5%) to three percent (3%) by weight in the mixture. The particles may then be pressed together to form the beads.

The beads are then disposed on the material 32 between the terminal pins 16 and the ferrule 20. The combination is then heated to a suitable temperature such as approximately 1225° F. for a suitable period of time such as a period to approximately thirty (30) minutes. The material then becomes fused to the terminal pins 16 and the ferrule 20. Since the combination is heated for only a relatively short period of time, the crystal structure of the material 34 is not changed significantly during the heating operation. The fusion of the material 34 to the ferrule 20 is facilitated by cooling the material rapidly in air.

The hermetic seal between the material 34 and the ferrule 20 is produced in various ways. For example, a thin polycrystalline layer is produced in the material at the boundary with the ferrule 20. For example, zinc silicate (Zn$_2$SiO$_4$) or a relatively complex compund of zinc, oxygen and silicon dioxide (2ZnO SiO$_2$) having the same chemical composition as zinc silicate or a combination of both is formed at such boundary. These crystals tend to become formed in the presence of lead or antimony. These zince compounds become crystallized in the form of Willemite crystals. Furthermore, crystals of zirconium silicate also become produced at such boundary.

The crystallization of the zirconium silicate occurs in the presence of lead. The crystallization of the zirconium silicate is facilitated by the inclusion of zinc zirconium silicate in the mixture since this compound tends to become dissolved at a lower temperature than zirconium silicate. Zinc zirconium silicate and zirconium silicate tend to exist as natural minerals and are preferably used in this form.

The Willemite crystals are of a different size and shape than the crystals of zirconium silicate. For example, the crystals of zirconium silicate tend to be smaller than the Willemite crystals. This causes nucleations of different sizes to be produced and facilitates the flexing and bending of the crystal layer adjacent the ferrule when subjected to thermal and mechanical shocks. In this way, the hermetic seal is maintained even when the material is subjected to severe thermal or mechanical shocks.

Zirconium spinel tends to increase the mechanical strength of the material. When introduced into the material, zirconium spinel is already in crystalline form so that it does not change as the material is heated and cooled as specified above. As a result, zirconium spinel acts as a filler in the material. Zirconium spinel tends to exist as a natural mineral and is preferably used in this form.

An oxygen valence bond is also produced between the material 34 and the ferrule 20 to facilitate the formation of a hermetic seal between them. This oxygen valence bond results from a chemical bond between oxygen atoms in the material and atoms on the surface of the ferrule 20. In other words, the oxygen is shared by the layer on the surface of the ferrule 20 and the material 34. This oxygen valence bond is produced during the heating of the material 34 and the ferrule 20 to the relatively high temperatures.

When an alloy of titanium is used as the ferrule 20, the alloy often has a composition of Ti6A14V. In other words, one (1) molecule of titanium is combined with six (6) molecules of aluminum and four (4) molecules of vanadium. Such an alloy is advantageous because the surface of the alloy tends to form oxides of titanium, vanadium and aluminum and these oxides tend to become bound to the material 34 by oxygen valence bonding. Thus, the inclusion of the other metals with titanium in the alloy tends to facilitate the hermetic seal with the material 34.

Because of the random orientation of the polycrystalline structure and the oxygen valence bonding of the oxygen to the external surface of the ferrule 20, the material 34 does not fragment or crumble in use, even when subjected to thermal and mechanical shocks. For example, any tendency for the material to crack occurs radially toward the terminal pins 16 so as to preserve the characteristics of the material in providing an electrical insulation.

The material 34 is also hermetically sealed to the terminal pins 16. For example, when the terminal pins 16 are made from platinum, the platinum tends to become chemically etched at its surface to a minor extent. This etching occurs from the action on the platinum, during the smelting and fusing operations, of the material constituting this invention. This etching may penetrate the surface of the platinum to a thickness of approximately one half mil (0.0005") to one mil (0.001") when the terminal pins 16 have a thickness of approximately thirty mils (0.030"). The material 34 then tends to become locked in the irregular surface produced in the surfaces of the terminal pins 16 as a result of such penetration.

The bond between the platinum terminal pins 16 and the material 34 is actually quite thin in physical dimensions. This bond has a thickness in the order of twenty Angstroms (20 A). The material 34 at the surfaces of the platinum terminal pins 16 tends to be more amorphous than the material at the surface of the ferrule 20, particularly when the ferrule is made from titanium or a titanium alloy.

With progressive distances from the ferrule 20, the material 34 becomes progressively amorphous. Thus, the material 34 may be almost entirely crystalline at the boundary with the ferrule 20. However, at positions somewhat removed from the ferrule 20, the material 34 may be predominantly amorphous.

The combination of amorphous and crystalline properties for the material 34 provides certain advantages in addition to those discussed above. For example, the crystalline structure in the ferrule 20 normally has an alpha ($\alpha$) phase at relatively low temperature but the characteristics of the crystalline structure change from the alpha ($\alpha$) phase to the beta ($\beta$) phase as the temperature of the material increases from approximately 800° F. to approximately 1400° F. For example, the coefficient of thermal expansion of the crystalline structure in the beta ($\beta$) phase is different from that in the alpha ($\alpha$) phase.

The partially amorphous characteristics of the material 34 tend to compensate for effects resulting from a transition in the crystalline structure between the alpha ($\alpha$) phase and the beta ($\beta$) phase. The interleaved characteristics of the polycrystalline structure at the boundary with the ferrule 20 also tend to compensate for any changes in the crystalline structure of the ferrule 20 between the alpha ($\alpha$) phase and the beta ($\beta$) phase.

The titanium alloy also has alpha ($\alpha$) and beta ($\beta$) phases. However, these phases are stabilized so that each phase exists over a relatively wide range of temperatures. These different phases are partially instrumental in causing the titanium alloy to be stronger than pure titanium. This is particularly true when the titanium alloy is heat treated.

The phase of the titanium alloy changes from alpha ($\alpha$) to beta ($\beta$) at a temperature of approximately 1300° F. However, a relatively long period of time at a temperature of approximately 1300° F. is required for the titanium alloy to change from the alpha ($\alpha$) phase to the beta ($\beta$) phase. The coefficient of thermal expansion of the titanium alloy in the alpha ($\alpha$) phase is different from that in the beta ($\beta$) phase.

The partially polycrystalline structure of the material 34 facilitates the retention of a hermetic seal as the titanium alloy changes from the alpha ($\alpha$) phase to the beta ($\beta$) phase. This results from the ability of the polycrystalline layer to adapt to differences in the expansion characteristics of the titanium alloy with changes in temperature. The oxygen valence bond between the ferrule 20 and the material 34 also facilitates the maintenance of the hermetic seal under such circumstances.

The material 34 is highly resistant to strong acids and alkalis. As will be appreciated, this is important when the material 34 is used in a heart pacemaker since the heart pacemaker is generally disposed in the body of a patient and is accordingly subjected to the fluids in the body of the patient. The material 34 also provides other advantages of some importance. For example, the material provides a high dielectric constant considerably greater than that of most other materials now in use. By way of illustraion, the electrical insulation between the terminal pins 16 and the ferrule 20 is as high as $10^{18}$ ohms. This is important in such equipment as heart pacemakers which have to operate satisfactorily under all of the adverse circumstances which a human body is capable of producing.

The material 34 also has other advantages of some importance. For example, when the operation of hermetically sealing the terminal pins 16 and the ferrule 20 has been completed, tests are made to determine if a hermetic seal has actually been produced. If a hermetic seal has not been produced, the combination of the terminal pin, the ferrule and the material may be fused at the temperature of approximately 1225° F. for an additional period to approximately thirty (30) minutes. Since the material is still somewhat amorphous, this additional fusing operation tends to facilitate the creation of the oxygen valence bond between the material and the ferrule. It also tends to facilitate the creation of a polycrystalline structure in the material, particularly at the surface adjacent the ferrule. As a result, any failure to produce a hermetic seal tends to become corrected.

The members 34a and 34b in FIG. 4 may be respectively provided with the following compositions:

| Material | Relative Amounts in Mixture | |
|---|---|---|
| | Member 34a | Member 34b |
| Zirconium silicate | 6.8 | 6.8 |
| Zinc zirconium silicate | 3.4 | 3.4 |
| Boric acid | 14.0 | 14.0 |
| Zirconium spinel | 3.4 | 3.4 |
| Red lead | 61.3 | 61.3 |
| Bismuth Trioxide | 6.8 | 6.8 |
| Quartz | 4.3 | 0 |
| Fusing temperature | 1200° F. | 1160° F. |

As will be seen, the fusing temperature of the material 34b is slightly below the fusing temperature of the material 34a. Further adjustments may be made to provide the material 34c with a lower melting temperature than the material 34b.

In another embodiment of the member, a terminal pin may be disposed within an annular ferrule in spaced relationship to the ferrule. The terminal pin may be made from a suitable material such as steel having a higher coefficient of thermal expansion than the terminal pin.

Although this application has been disclosed and illustrated with reference to particular applications, the principles involved are susceptible of numerous other applications which will be apparent to persons skilled in the art. The invention is, therefore, to be limited only as indicated by the scope of the appended claims.

I claim:

1. In combination, a lid, a ferrule made from a material having a coefficient of thermal expansion which changes at a particular rate with changes in temperature, the ferrule being attached to the lid and including a body portion constructed for pivotal movement at a particular position along the body portion, a first ceramic material disposed within the ferrule and having hard and rigid properties and supported by the ferrule and partially fused to the ferrule, a second ceramic material disposed in the ferrule on the first ceramic material and fused to the first ceramic material and the ferrule and having partially amorphous and partially crystalline properties and having a coefficient of thermal expansion which changes at substantially the particular rate with changes in temperatures, an insulating member disposed on the second ceramic material and fused to the second ceramic material and having a coefficient of thermal expansion which changes at substantially the particular rate with changes in temperture, and a terminal pin extending through the first and second ceramic materials, the insulating member, the ferrule and the lid in insulated relationship to the ferrule and the lid.

2. The combination set forth in claim 1, including, the first ceramic material being substantially crystalline.

3. The combination set forth in claim 1 wherein the insulating member has a groove in its external periphery and at least a pair of terminal pins are extended through the ferrule and the lid and are disposed on opposite sides of the groove.

4. The combination set forth in claim 3 wherein the first ceramic material is substantially crystalline.

5. The combination set forth in claim 1 wherein the second ceramic material is formed from a plurality of layers each having the same chemical components but in different proportions to provide progressively increased amorphous characteristics to the different layers.

6. The combination set forth in claim 1 wherein the ferrule has a ledge at a position along the body portion and the construction of the ferrule to obtain the pivotal movement is in the form of a heat sink at a position between the lid and the ledge for localizing the heat produced during the attachment of the ferrule to the lid.

7. The combination set forth in claim 6 wherein the first ceramic material is incompletely attached to the ledge of the ferrule to provide for compensations between the positioning of the ferrule and the first ceramic material in accordance with the introduction of heat to the heat sink of the ferrule.

8. In combination, a lid, a hollow ferrule attached to the lid and having properties of flexing in response to stresses in the ferrule, the ferrule having an internal ledge, a first insulating material disposed in the ferrule and supported on the ledge in a relationship to provide for adjustments in the position of the first insulating material relative to the ledge as a result of stresses in the ferrule, a second insulating material disposed in the ferrule on the first insulating material in hermetically sealed relationship to the first insulating material and to the ferrule and having properties to maintain the hermetically sealed relationship with the ferrule and the first insulating material even with stresses in the ferrule, a third insulating material disposed in the ferrule on the second insulating material in hermetically sealed relationship to the second insulating material and having properties to maintain the hermetically sealed relationship with the second insulating material even with stresses in the ferrule, and at least one terminal pin extending through the ferrule and the lid and the first, second and third insulating materials and hermetically sealed to at least the second and third insulating materials.

9. The combination set forth in claim 8 wherein the stresses in the ferrule result from heat and the adjustable relationship between the first insulating material and the ferrule result from an incomplete hermetic seal between the first insulating material and the ferrule.

10. The combination set forth in claim 9 wherein the ferrule and the second and third insulating materials have substantially the same coefficient of thermal expansion.

11. The combination set forth in claim 10 wherein the ferrule constitutes titanium or a titanium alloy and the third insulating material constitutes Fosterite.

12. The combination set forth in claim 8 including, a heat sink defined in the ferrule by a cut in the ferrule.

13. The combination set forth in claim 12 including, there being a cruciform groove in the third insulating material to define a plurality of different sectors in the third insulating material, and
a plurality of additional terminal pins each extending through the ferrule and the lid and the first, second and third insulating materials and hermetically sealed to an individual section of the third insulating material and to the first and second insulating materials.

14. In combination,
a lid,
a hollow ferrule attached to the lid and having a heat sink and being adjustable in position upon the introduction of heat to the ferrule to attach the ferrule to the lid,
a terminal pin extending through the ferrule and the lid in spaced relationship to the ferrule and the lid,
first insulating means disposed in the ferrule for providing for an adjustment in the position of the ferrule without the introduction of heat to the ferrule, and
second insulating means disposed in the ferrule and hermetically sealed to the first insulating means, the terminal pin and the ferrule.

15. The combination set forth in claim 14 wherein the second insulating means include an insulating material impervious to stresses from heat and having a coefficient of thermal expansion which changes at a rate, with changes in temperature, closely approximating the rate of change of the coefficient of thermal expansion of the ferrule with such changes in temperature.

16. The combination set forth in claim 14 wherein the first insulating means include an insulating material impervious to mechanical shock and incompletely sealed to the ferrule to provide for adjustments in the position of the ferrule upon the introduction of heat to the ferrule.

17. The combination set forth in claim 16 wherein the second insulating means has a coefficient of thermal expansion which changes at approximately the same rate as the rate of change of the coefficient of thermal expansion of the ferrule with changes in temperature.

18. In combination,
a lid,
a ferrule having a flange portion attached to the lid and having a body portion extending from the flange portion in transverse relationship to the flange portion,
there being a heat sink in the body portion of the ferrule,
a shelf in the ferrule at a position further removed from the flange portion than the heat sink,
an insulating member disposed in the ferrule on the shelf and incompletely sealed to the shelf to provide for a flexible relationship between the ferrule and the insulating member,
insulating means disposed on the insulating member in hermetically sealed relationship to the insulating member, and
at least one terminal pin extending through the lid, the ferrule, the insulating means and the insulating member and having an insulating relationship to the lid and the ferrule.

19. The combination set forth in claim 18, including, the ferrule and the insulating means having coefficients of thermal expansion which change at substantially the same rate with changes in temperature.

20. The combination set forth in claim 19 including, the heat sink constituting a thinned section of the body portion of the ferrule and
the insulating member including an insulating material having substantially crystalline properties and having hard and rigid properties.

21. The combination set forth in claim 18 wherein the insulating means includes at least one layer of an insulating material having partially amorphous and partially crystalline properties.

22. The combination set forth in claim 18, wherein the insulating means include a member having at least one groove at its periphery to define at least a pair of different sections and
at least an additional terminal pin, individual ones of the terminal pin and the additional terminal pin extending through different ones of the sections of the grooved insulating member and through the incompletely sealed insulating member and the ferrule.

23. The combination set forth in claim 18 wherein the insulating means include a plurality of stacked layers of insulating material each having partially amorphous and partially crystalline properties and each having a disposition progressively displaced from the shelf and each of the layers progressively displaced from the shelf being more amorphous than the layers closer to the shelf.

24. The combination set forth in claim 23, including, the insulating means including a member having at least a pair of grooves at its periphery to define a plurality of different sections and a plurality of additional terminal pins, individual ones of the terminal pin and the additional terminal pins extending through different ones of the sections of the grooved insulating member and through the incompletely sealed member and the ferrule.

* * * * *